(12) United States Patent
Domaschko et al.

(10) Patent No.: US 8,064,050 B2
(45) Date of Patent: Nov. 22, 2011

(54) METHOD OF USING A FLOW CELL APPARATUS FOR VISUALIZING ADDITIVE DEPOSITION ON A SUBSTRATE

(75) Inventors: Dirk Wilhelm Domaschko, Hamilton, OH (US); Renee Danielle Bolden, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 313 days.

(21) Appl. No.: 12/504,017

(22) Filed: Jul. 16, 2009

(65) Prior Publication Data

US 2011/0013183 A1    Jan. 20, 2011

(51) Int. Cl.
*G01N 21/01* (2006.01)
*G01N 1/10* (2006.01)

(52) U.S. Cl. ........................................ 356/246; 356/244

(58) Field of Classification Search ........... 356/244–246
See application file for complete search history.

(56) References Cited

U.S. PATENT DOCUMENTS

| | | | |
|---|---|---|---|
| 4,804,267 A | 2/1989 | Greenfield | |
| 4,974,952 A | 12/1990 | Focht | |
| 6,444,982 B1 | 9/2002 | Mitchell | |
| 6,836,559 B2 | 12/2004 | Abdel-Fattah | |
| 7,304,739 B2 * | 12/2007 | Grossinger et al. | 356/402 |
| 7,595,868 B2 * | 9/2009 | Korotkov | 356/237.1 |
| 2002/0039797 A1 | 4/2002 | Bonde | |
| 2003/0133119 A1 | 7/2003 | Bachur, Jr. | |

FOREIGN PATENT DOCUMENTS

EP         252762 A1      1/1988

OTHER PUBLICATIONS

Amr I. Abdel-Fattah, Automated Video Microscopic Imaging and Data Acquisition System for Colloid Deposition Measurements, Journal of Colloid and Interface Science 264, 241-258, 2002.

* cited by examiner

*Primary Examiner* — Michael P Stafira
(74) *Attorney, Agent, or Firm* — Laura R. Grunzinger

(57) ABSTRACT

A method of visualizing the deposition of an additive from a personal care composition onto substrates such as hair, skin mimic and fabric through the use of a flow cell device.

18 Claims, 4 Drawing Sheets

METHOD OF USING A FLOW CELL APPARATUS FOR VISUALIZING ADDITIVE DEPOSITION ON A SUBSTRATE

FIELD OF THE INVENTION

The present invention relates to a method of using a flow cell apparatus for visualizing additive deposition of an additive onto a substrate surface, such as hair, skin mimic or fabric.

BACKGROUND OF THE INVENTION

Measuring and visualizing particle deposition onto substrates is very important for a variety of industries. Medical techniques have been developed to assess foreign particle deposition on lung tissues, and to evaluate risks of blockages to blood vessels. Methods have been developed for determining deposition rates of charged particles onto substrates for the purpose of measuring electrostatic attraction. Computer simulations have also been used in order to observe particle deposition as a means of measuring air filter efficiency. These techniques generally provide quantitative data to describe their results. Interpreting this data typically requires either specialized training in the relevant field, or some secondary processing to communicate trends and effects. Therefore, these techniques do not provide an efficient means for communicating benefits or detriments based on particle deposition onto substrates. Also, none of these techniques provide an environment where particle deposition may be observed as various additives are introduced into a system.

Flow cell units are known (see U.S. Pat. No. 4,974,952), and are often used to introduce various drugs and additives into a fluid environment to analyze their effects. Generally, flow cell units are applied to an array of biological research applications. Flow cells are commonly used in flow cytometer configurations. Such devices may be used to analyze several thousand particles per second, and can actively separate and isolate particles having specified properties. Flow cytometry is most commonly associated with cellular biological applications such as fluorescence-activated cell sorting. However, the technology has also been broadly applied to medical and bioengineering experimentation as well.

Attempts have been made to use flow cells to visualize particle deposition on substrates. Previous attempts to apply the technology to particle-substrate visualization have used flow cell DIC microscopy to visualize coacervate interaction with hair fibers. J. Cosmet. Sci., 58, 637-650 (November/December 2007). Coacervate phases are important to aid in deposition of conditioning particles to hair fibers, and flow cell DIC microscopy is useful for visualizing deposition efficiency of various personal care compositions on the hair substrate.

However, previous flow cell designs position the hair fiber between two slides, through which a liquid solution is caused to flow. This configuration results in an inefficient system, in that the liquid solution cannot flow around the entire hair fiber because the fiber is "sandwiched" between the two flow cell slides, being in contact with both. Therefore, the liquid solution can only interact with the edges of the substrate which are not in contact with the slides. Accordingly, during analysis, only the edges of the visible substrate are exposed to the liquid solution, and visualization suffers. Furthermore, "sandwiching" often causes additives to deposit onto the surface of the slides, as there is insufficient spacing to allow for some particles to pass through the system. Therefore, deposition onto the substrate becomes indistinguishable from other intervening additives.

Based on the foregoing, there is a need for a flow cell apparatus which provides a means for visual analysis of particle-substrate interaction, whereby a greater surface area of the substrate is exposed for analysis.

SUMMARY OF THE INVENTION

The present invention relates to a method for visualizing additive deposition comprising the steps of: (a) preparing a diluent comprising a personal care composition and water, the personal care composition comprising an additive; (b) placing a substrate into a flow cell, the flow cell comprising a flow cell chamber and a flow path, the flow cell chamber comprising a fluid volume capacity and four or more flow cell chamber walls; the substrate is suspended within the flow cell chamber such that the substrate does not contact more than two of the flow cell chamber walls and the substrate is within the flow path; (c) injecting the diluent into the flow cell; (d) recording a visual image of the flow cell chamber.

BRIEF DESCRIPTION OF THE DRAWINGS

The accompanying drawings illustrate embodiments of the invention and, together with a general description of the invention given above, and the detailed description given below, serve to explain the invention.

DETAILED DESCRIPTION OF THE INVENTION

Figure 1:
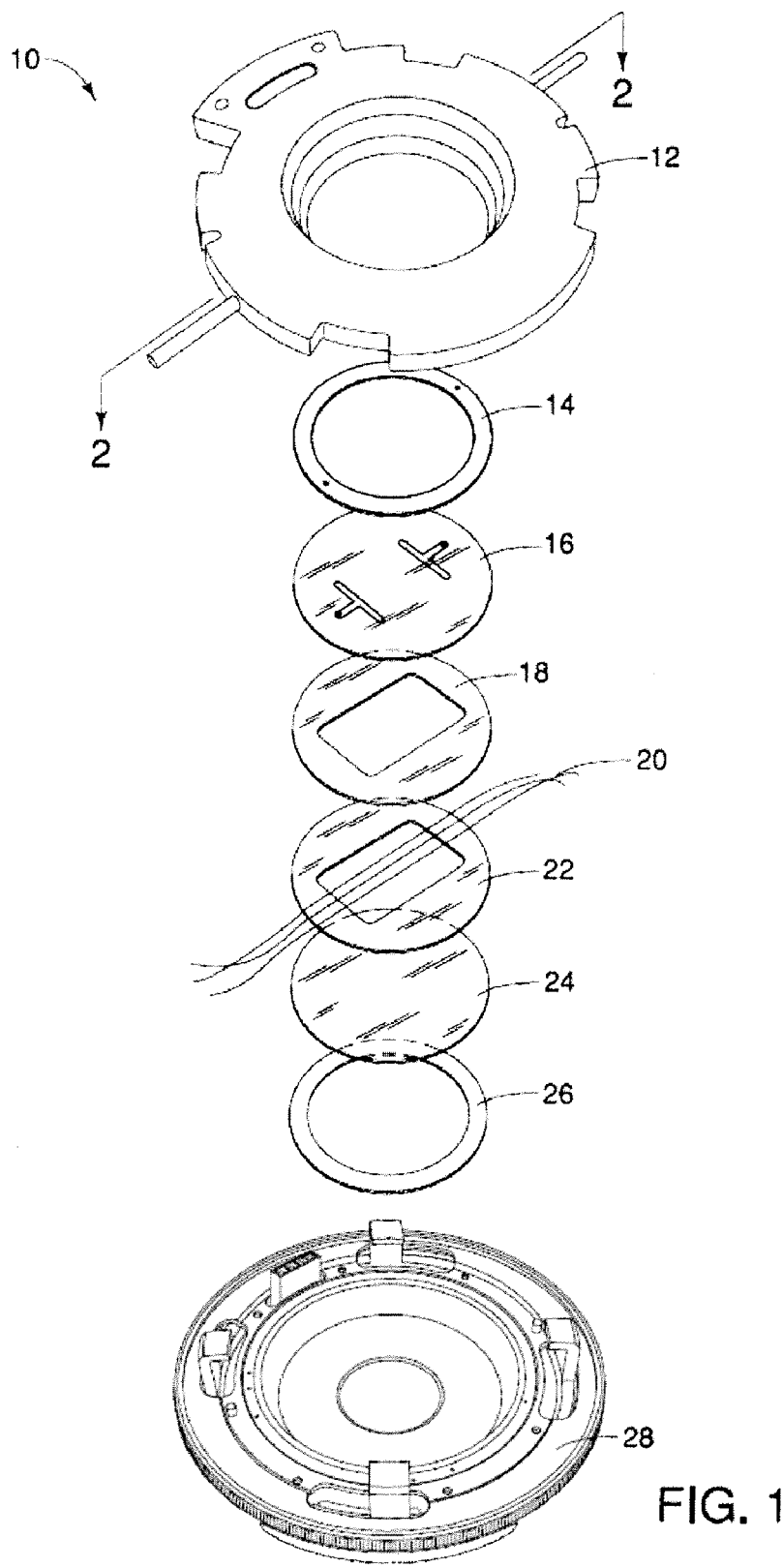
FIG. 1 is a an exploded view of the flow cell apparatus.

The present invention relates to a method for visualizing particle deposition comprising the steps of preparing a diluent comprising an additive, placing a substrate into a flow cell comprising a flow cell chamber and a flow path, injecting the diluent into the flow cell and recording a visual image of the flow cell chamber.

The careful control of the flow ratio of the diluent into the flow cell chamber and the selection of the fluid volume capacity of the flow cell chamber create an environment that visual images of additives being deposited onto a substrate.

Diluent

Personal care compositions are often sold to consumers in a form that is further diluted by the consumer during use. For example, shampoo and conditioner compositions are often dispensed to the hand of the user and then applied to the hair. During use, water is often added to the hair thus mixing with and diluting the shampoo and conditioner composition, often referred to as "in-use" conditions. Therefore, a dilution ratio should be chosen to reflect actual consumer conditions when the personal care composition is used to form a diluent for use in the present method.

The dilution ratio of the personal care composition will depend on the viscosity and rheology of the personal care composition in question, but it should be sufficiently diluted such as not to impede the transmission of the diluent through the flow cell path.

Further, the dilution ratio must be selected such that that diluent can be "seen" within the flow cell chamber (discussed below). Examples of what can be "seen" can be seen in FIG. 4A. "Seen" is used herein to mean that the diluent and the additive in the diluent are visible with magnifying means and not necessarily via the naked eye.

A dilution ratio of the liquid composition to water should be from about 1:1 to about 1:150, more preferably 1:2 to about 1:50 and most preferably from about 1:2 to about 1:9. In one embodiment a shampoo composition is formed into a diluent by mixing the composition in a composition:water ratio from about 1:2 to about 1:10, such as 1:9. In one embodiment a conditioner composition is formed into a diluent by mixing the composition in a composition:water ratio from about 1:70 to about 1:150, such as 1:100. In one embodiment a skin care composition, such as a body wash, is formed into a diluent by mixing the composition in a composition:water ratio from about 1:1 to about 1:10, such as 1:2 or 1:9. In one embodiment a fabric care composition, such as a fabric softener, is formed into a diluent by mixing the composition in a composition:water ratio of from about 1:1 to about 1:100.

Additive

The term, "additive" as used herein, means any element which is present in the fluid which is caused to flow through the flow cell path, and which is visually distinguishable from the surrounding fluid when viewed through a microscope or other magnifying device. These additives are best characterized as being the materials from which the particular benefit (e.g., conditioning, softness, moisturization, volumization) derived from using the personal care composition.

For example, in hair care compositions such as shampoo compositions, skin care compositions such as body wash compositions and in fabric care compositions, coacervates are often utilized to provide a vehicle for actives that give conditioning, moisturizing or softening benefits. Coacervates in shampoo compositions are formed upon dilution and is the associative phase separation that occurs when an anionic surfactant interacts with a cationic polymer at a critical association constant. See for further information *Polymer-Surfactant Interaction*, edited by Jan C. T. Kwak, Surfactant Science Series Vol. 77, Marcel Dekker, Inc. New York (1998). The coacervate with additives such as silicones then deposit onto the surface of hair. As such, in one embodiment, the additive may be considered a coacervate with or without silicone materials.

Skin care compositions utilize coacervates with petrolatum materials. Fabric care compositions also utilize silicone materials.

In conditioner compositions utilize a fatty alcohol and surfactant gel network in combination with silicone materials. See US 2006/0078528A1

Suitable materials for the additive include those discussed in US 2007/0207109A1, US 2005/01582661A1, US 2006/0024381A1, US 2007/0010408A1, US7528099B2.

However, the additive may also be deposited onto a surface by a mechanism known as filtration where the mechanical movement or flow of the diluent over the surface of the substrate causes the additive to make contact with and remain on the surface of the substrate.

Substrates

Suitable substrates for use in the method herein include hair strands, skin mimic and fabric samples. The substrate is orientated within the flow cell chamber to come into contact with the flow path. Dependent upon the substrate, the orientation of the substrate within the flow cell chamber (discussed below) will affect how the additive is being deposited onto the substrate surface. In one embodiment, a single hair or a plurality of hairs are utilized as the substrate. The hair or hairs are axially orientated to extend from one end of the flow cell chamber to the other in the direction of the flow path of the diluent to see deposition effects of the diluent onto the hair surface. In another embodiment, a plurality of hairs is axially oriented perpendicular to the flow path of the diluent to see filtration effects of the diluent onto the hair surface.

Hair strands or a plurality of hair strands may be utilized as the substrate. Virgin hair samples (non-chemically altered hair) and damaged hair samples may be used depending upon the type of visualization desired (i.e., deposition of additives on virgin and/or damaged hair). Hair switches are commercially available, such as those available from Hugo Royer International Limited (10 Lakeside Business Park, Sandhurst, Berkshire, GU47 9DN, England).

Skin mimic may be utilized as a substrate particularly when utilizing a skin care composition such as a body wash. Further information regarding skin mimic may be found in WO08/084442A1.

Fabric—natural, synthetic or mixed natural/synthetic fibers may be used, such as silk, wool, cotton, rayon, nylon, polyesters, lycra, and spandex.

Flow Cell

Flow cells are known such as the device described in U.S. Pat. No. 4,974,952 and are commercially available such as the Focht Flow Cell available from Bioptechs. A suitable flow cell (10) is shown as an exploded view in FIG. 1. The flow cell (10) comprises a chamber frame (12), an upper gasket (14), a micro-aqueduct slide (16), a first spacer (18), a substrate (20), a second spacer (22), a glass slide (24), a lower gasket (26) and a support plate (28). The flow cell (10) must be selected such that it can hold a substrate within a flow cell chamber (32), provides a flow path (30) and be arranged such that light can pass through the flow cell (10) and the flow cell chamber (32). As such, the chamber frame (12), upper gasket (14), micro-aqueduct slide (16), first spacer (18), second spacer (22), glass slide (24), lower gasket (26) and support plate (28) are selected such that at least a portion of these components are contain a central aperture or comprise a transparent area. Further, the central apertures or transparent areas of these components align along a similar vertical axis through the flow cell (10) such that light can pass through the flow cell (10). In one embodiment, the first gasket (18) and second gasket (22) comprise a central aperture such that the first gasket (18) and the second gasket (22) have an internal edge and an external edge and that the internal edge is concentric with the external edge.

Figure 2:
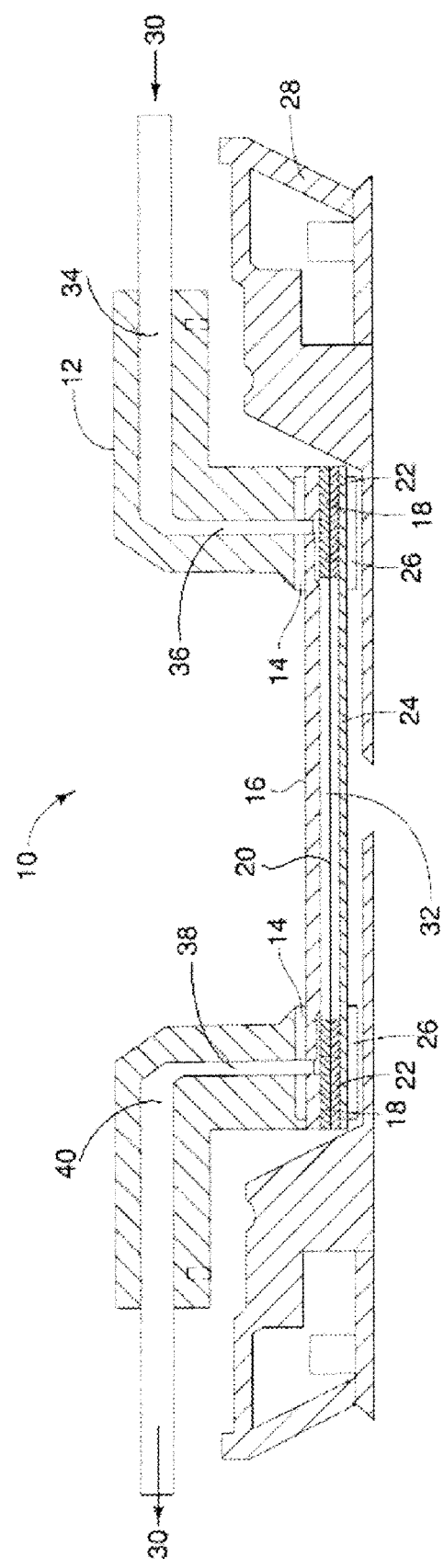
FIG. 2 is a cross sectional view of the micro-aqueduct slide according to the arrows 2-2 of FIG. 1.

The flow cell (10), when assembled proves a flow path (30) for the diluent to be injected into a flow cell chamber (32), travel through the flow cell chamber (32) and then exit the flow cell chamber (32). The flow path (30) and flow cell chamber (32) can be seen in FIG. 2. The flow path comprises an in-flow tube (34) at least partially extending from and at least partially contained within the chamber frame (12), the in-flow tube (34) is connected to a vertical in-flow tube (36) at least partially contained within and at least partially extending from the chamber frame (12); the vertical in-flow tube (36) is in fluid communication with the flow cell chamber (32); the flow cell chamber (32) is in fluid communication with a vertical out-flow tube (38) at least partially contained within and at least partially extending from the chamber frame (12); the vertical out-flow tube (38) is connected to an out-flow tube (40) at least partially extending from and at least partially contained within the chamber frame (12).

It is important to achieve a laminar flow of the diluent within the flow cell chamber (32). In one embodiment, this is achieved through the use of the micro-aqueduct slide (16) which comprises a pair of opposed shallow fluid grooves formed on the surface of the micro-aqueduct slide (16) such as by etching, or the like. In one embodiment, the shallow fluid grooves are T-shaped which are spaced from one another and disposed such that the stems of the T-shaped shallow fluid grooves are axially aligned with one another, while the tops of the T-shaped shallow fluid grooves are disposed in a parallel relationship to one another.

The shallow fluid grooves of the micro-aqueduct slide (16) further provide part of the structure for the flow path (30) for the diluent. The diluent is injected by an injecting means, such as a syringe pump, into an end of the in-flow tube (34) traveling through the in-flow tube (34) to the vertical in-flow tube (36) then traveling through the vertical in-flow tube (36). The vertical in-flow tube (36) extends from the bottom side of the chamber frame (12) and extends through a fluid aperture in the upper gasket (14) and through a fluid aperture in the micro-aqueduct slide (16). The fluid aperture in the micro-aqueduct slide (16) is located at the terminal end of the stem of the T-shaped shallow fluid groove.

A flow cell chamber (32) is a space created by the micro-aqueduct slide (16), the first spacer (18), the second spacer (22) and the glass slide (24). There are four or more walls of the flow cell chamber (32). In one embodiment there are four walls consisting of the bottom side of the micro-aqueduct slide (16), the internal edges of the aperture of the first spacer (18) and the second spacer (22) and the top side of the glass slide (24).

The substrate (20) is intended to be within the flow cell chamber (32), but suspended such that the substrate (20) does not touch all of the walls of the flow cell chamber (32). In one embodiment, the substrate is suspended by being held between the first spacer (18) and the second spacer (22) at two different locations on the internal edges of the first spacer (18) and second spacer (22), thereby traversing the apertures, but not touching the bottom of the micro-aqueduct slide (16) or the top of the glass slide (24).

The diluent continues on the flow path (30) from the vertical in-flow tube (36) into the flow cell chamber (32) via the shallow fluid groove of the micro-aqueduct slide (16). The diluent then passes the substrate (20) and exits the flow cell chamber (32) via the oppositely located shallow fluid groove of the micro-aqueduct slide (16) comprising a fluid aperture in the micro-aqueduct slide (16) which is located at the terminal end of the stem of the oppositely located T-shaped shallow fluid groove. The flow path (30) continues from the fluid aperture in the micro-aqueduct slide (16) into a terminal end of the vertical out-flow tube (38) which extends from the bottom side of the chamber frame (12) and extends through the fluid aperture in the micro-aqueduct slide (16) and through a fluid aperture in the upper gasket (14). The diluent travels through the vertical out-flow tube (38) to the out-flow tube (40) and then traveling through the out-flow tube (40) to then exit the flow cell (10).

The flow cell chamber (32) should have a fluid volume capacity of from about 0.05 ml to about 100 ml, preferably from about 0.1 ml to about 50 ml, and most preferably from about 0.1 ml to about 10 ml. These ranges have been found to promote laminar flow and provide a stable environment (laminar flow) for observing particle deposition. The volume of the flow cell chamber (32) will be affected by the thickness of the first spacer (18) and the second spacer (22) and the size of the central apertures of the spacers (18, 22).

Gasket/Spacer Thickness

The fluid volume capacity of the flow cell chamber (32) can be adjustable and selected such that the spacing between the substrate (20) and the surfaces of the micro-aqueduct slide (16) and the glass slide (24) is such that the substrate (20) is not touching more the two walls of the flow cell chamber (32). The first spacer (18) and second spacer (22) should respectively have a thickness of at least about 0.1 mm, more preferably at least about 0.25 mm, and most preferably at least about 0.50 mm. Further, the first spacer (18) and second spacer (22) should respectively have a thickness of less than about 1.5 mm, preferably less than about 1.0 mm, and most preferably less than about 0.50 mm. The flow cell chamber (32) should also have a fluid volume capacity which is generally close to, or identical to the volume of the diluent entering into the flow cell chamber (32), in order to promote laminar flow as described hereinafter.

Flow Rate

The flow rate of the diluent into the flow cell (10), and preferably into the flow cell chamber (32), should be maintained at from about 0.1 ml/min to about 0.5 ml/min, more preferably from about 0.2 ml/min to about 0.4 ml/min, and most preferably from about 0.2 ml/min to about 0.3 ml/min.

The flow rate is affected by the inside diameter and length of the in-flow tube (34), vertical in-flow tube (36), vertical out-flow tube (38) and out-flow tube (40). Any dead volume (such as that arising from angled directions in the aforementioned tubes) should also be taken into account.

The in-flow tube (34) and out-flow tube (40), in one embodiment, have the same length and inside diameter. The tube length of the in-flow tube (34) and out-flow tube (40) may be from about 20 mm to about 40 mm, more preferably from about 25 mm to about 35 mm, most preferably about 29 mm. The inside diameter of in-flow tube (34) and out-flow tube (40) may be from about 0.5 mm to about 2 mm, more preferably about 1 mm to about 1.6 mm, most preferably about 1.57 mm.

The vertical in-flow tube (36) and vertical out-flow tube (38), in one embodiment, have the same length and inside diameter. The tube length of the vertical in-flow tube (36) and vertical out-flow tube (38) may be from about 5 mm to about 20 mm, preferably from about 7 mm to about 15 mm, preferably about 10 mm. The inside diameter of the vertical in-flow tube (36) and vertical out-flow tube (38) may be from about 0.5 mm to about 1 mm, preferably from 0.6 mm to about 0.9 mm, preferably about 0.88 mm.

Optional Step

The method herein may further comprise the step of injecting water into the flow cell (10) in the same fashion that the diluent is injected into the flow cell (10). The step of injecting water further replicates the "in-use" conditions of consumers and can be equated to the rinsing of the personal care composition from the substrate. The flow rate of the water into the flow cell (10) should be maintained at from about 0.1 ml/min to about 0.5 ml/min, more preferably from about 0.2 ml/min to about 0.4 ml/min, and most preferably from about 0.2 ml/min to about 0.3 ml/min.

Recording Step

The recordation of a visual image of the flow cell chamber should include a visual image of at least a portion of the substrate. The recordation may be accomplished by any means for still or dynamic visual recordation such as a digital camera or video camera. In order to assist in the capture of a visual image a light source should be utilized such that light passes through the flow cell (10), preferably directed from the light source though the flow cell (10) from the support plate (28) of the flow cell (10) and the recordation device is located on the chamber frame (12) of the flow cell (10). Therefore the method may further comprises the step of lighting the flow cell from a light source though the flow cell to a recordation device located on the opposite side of the flow cell from the light source. Examples of visual images captured for the method described can be seen in FIGS. 3A-4B.

Figure 3A:
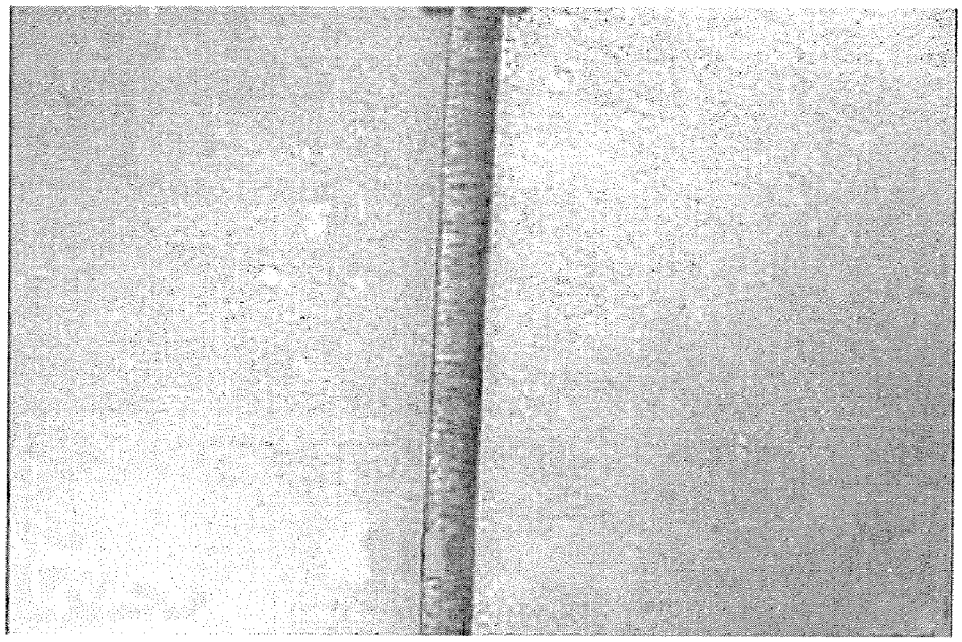
FIG. 3A is an image taken during the operation of the flow cell unit herein, in the presence of a shampoo composition.

FIG. 3A is an image taken during the method described above wherein the personal care composition a shampoo composition shown below in Table 1 which has been diluted with water in a shampoo composition to water ratio of 1:9. The diluent is injected at a flow rate of 0.2 ml/min.

Figure 3B:
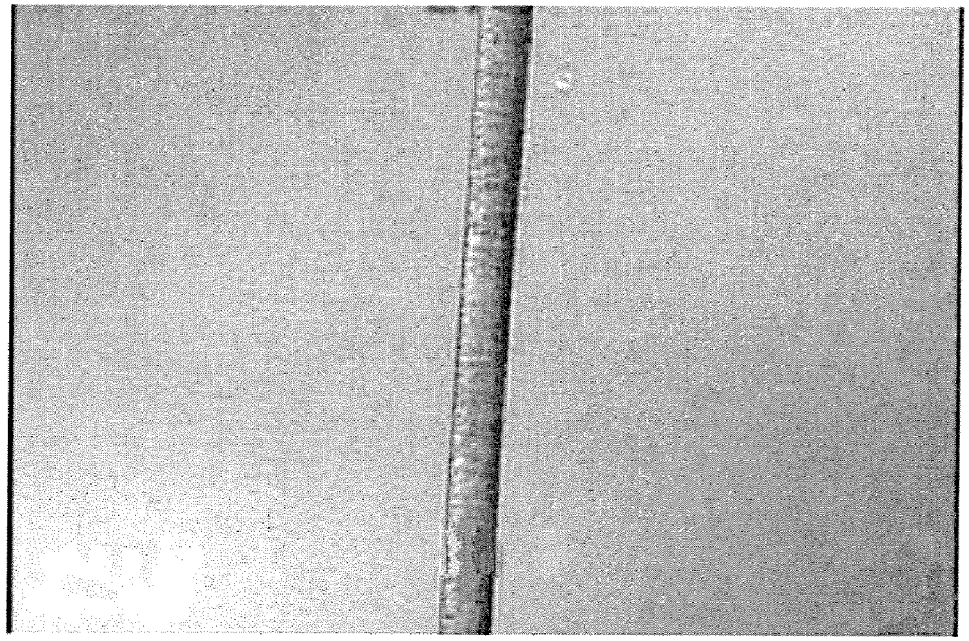
FIG. 3B is an image taken during the operation of the flow cell unit herein, after flushing the shampoo composition of FIG. 3A from the flow cell unit.

FIG. 3B is an image taken during method described for FIG. 3A wherein the method comprises the optional step of injecting deionized water wherein the water is injected at a flow rate of 0.3 ml/min.

Figure 4A:
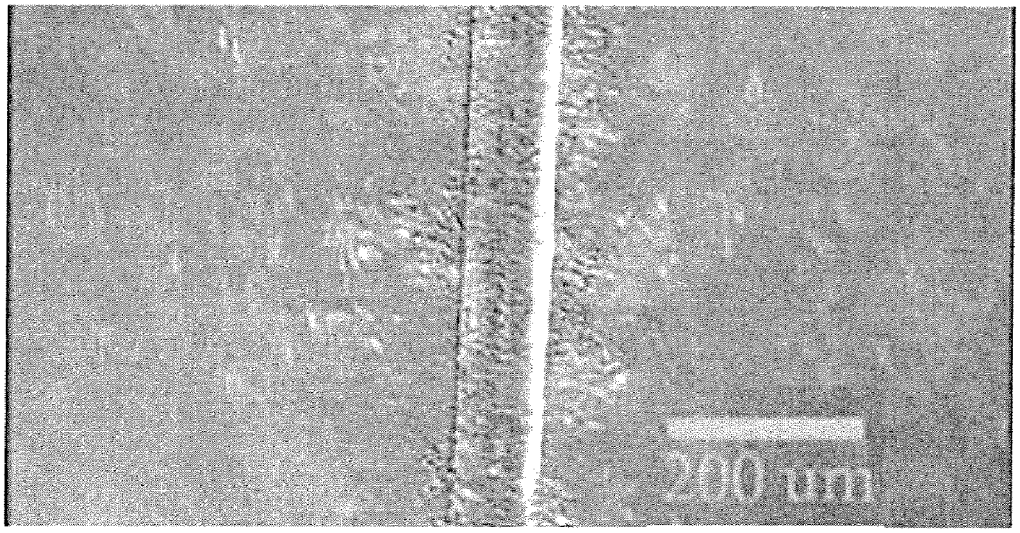
FIG. 4A is an image taken during the operation of the flow cell unit herein, in the presence of a shampoo composition which comprises particles and a deposition aid.

FIG. 4A is an image taken during the operation of the flow cell unit herein, in the presence of a shampoo composition shown in Table 2 below which comprises particles and a deposition aid which has been diluted with water in a shampoo composition to water ratio of 1:9. The diluent is injected at a flow rate of 0.2 ml/min.

Figure 4B:
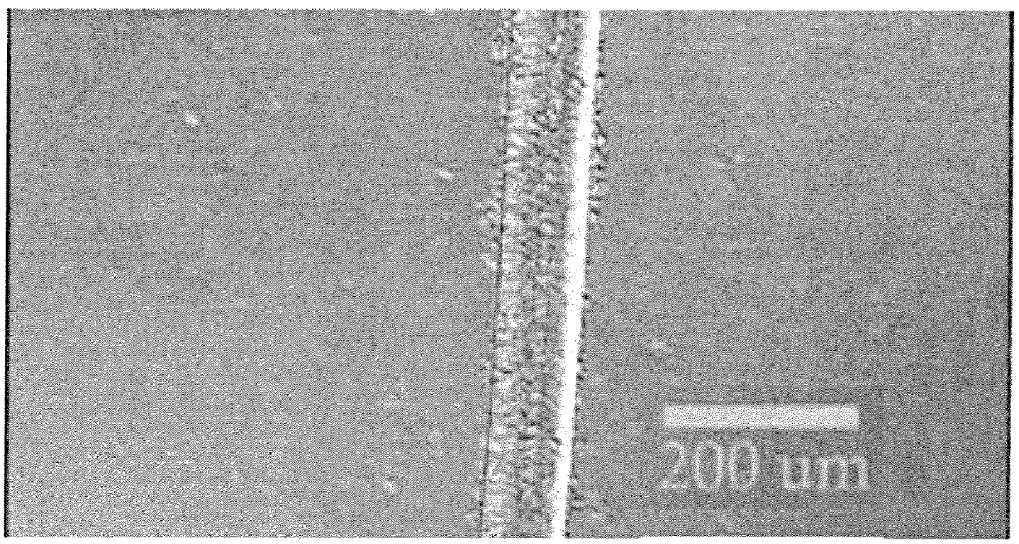
FIG. 4B is an image taken during the operation of the flow cell unit herein, after flushing the shampoo composition comprising particles and a deposition aid of FIG. 4A from the flow cell unit.

FIG. 4B is an image taken during the operation of the flow cell unit herein, after flushing the shampoo composition comprising particles and a deposition aid of FIG. 4A from the flow cell unit with deionized water wherein the water is injected at a flow rate of 0.3 ml/min.

As the diluent is introduced into the flow cell chamber (32), the additive can be seen as coacervate particles aggregating around, and depositing onto the substrate (20) of a single hair fiber in FIG. 4A, while little to no coacervate particles are seen in FIG. 3A. The method described herein provides a clear visual indication of particle deposition efficiency of a personal care composition.

Further, in replicating a "in-use" rinse situation when deionized water passes through the flow cell chamber (32), FIG. 4B shows that the particles of the shampoo diluent remain deposited onto the hair fiber substrate. Therefore, the method described herein is useful for observing and analyzing particle deposition efficiency onto the substrate. It is also important to note that the flow cell chamber (32) volume selection herein provides a clear view of particle deposition, not only along the edges of the substrate, but also allows for visualization of particle deposition on the entire visible surface of the hair fiber.

The enhanced viewable area of deposition is enabled by the increase of the flow cell chamber (32) volume by the use of the first spacer (18) and second spacer (22), which effectively suspends the substrate (20) from contacting the micro-aqueduct slide (16) and the glass slide (24). After analysis within the flow cell (10), the substrate (20) can be removed from the flow cell (10) for any desired subsequent analysis, such as electron microscopy, to confirm quantitatively, the deposition of additives onto the substrate (20).

TABLE 1

| Ingredient | Wt % |
| --- | --- |
| Ammonium Lauryl Sulfate | 6.35 |
| Ammonium Laureth (3.0) Sulfate | 7.65 |
| Ethylene glycol distearate | 1.5 |
| Cocamide MEA | 0.8 |
| Cetyl alcohol | 0.9 |

TABLE 1-continued

| Ingredient | Wt % |
| --- | --- |
| Polyquaternium-10[1] | 0.25 |
| PEG7M | 0.1 |
| Dimethicone 330M | 3.35 |
| Water, fragrance, preservatives, minors | To 100 |

[1]Poly LR-30M ex Americol

TABLE 2

| Ingredient | Wt % |
| --- | --- |
| Sodium Lauryl Sulfate | 6.00 |
| Sodium Laureth (3.0) Sulfate | 6.00 |
| Cocamidopropyl Betaine | 1.00 |
| Cocamide MEA | 0.85 |
| Glycol Distearate | 1.50 |
| AM:Triquat[1] | 0.15 |
| Dimethicone | 2.00 |
| Citric Acid | 0.23 |
| Sodium Chloride | 1.05 |
| Water, fragrance, preservatives, and minors | To 100 |

[1]MIRAPOL ® AT-1 ex Rhodia

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for visualizing additive deposition comprising the steps of:
   (a) preparing a diluent comprising a personal care composition and water, the personal care composition comprising an additive;
   (b) placing a substrate into a flow cell, the flow cell comprising a flow cell chamber and a flow path, the flow cell chamber comprising a fluid volume capacity and four or more flow cell chamber walls; the substrate is suspended within the flow cell chamber such that the substrate does not contact more than two of the flow cell chamber walls and the substrate is within the flow path;
   (c) injecting the diluent into the flow cell;
   (d) recording a visual image of the flow cell chamber.

2. The method of claim 1 wherein the diluent comprises a dilution ratio of personal care composition and water of from about 1:1 to about 1:150.

3. The method of claim 1 wherein the flow path results in a laminar flow when the flow path is within the flow cell chamber.

4. The method of claim 1 wherein the flow cell chamber comprises four walls.

5. The method of claim 1 wherein the injection of the diluent is maintained at a flow rate of from about 0.1 ml/min to about 0.5 ml/min.

6. The method of claim 1 wherein the injection of the diluent is maintained such that a flow rate of the diluent into the flow cell chamber is of from about 0.1 ml/min to about 0.5 ml/min.

7. The method of claim 1 wherein the fluid volume capacity is from about 0.05 ml to about 100 ml.

8. The method of claim 1 further comprising the step of injecting water into the flow cell after the step of injecting the diluent.

9. The method of claim 8 wherein the injection of the water is maintained such that a flow rate of the diluent into the flow cell chamber is of from about 0.1 ml/min to about 0.5 ml/min.

10. The method of claim 1 wherein fluid volume capacity is adjustable and selected such that the distance between the substrate and the flow cell chamber walls not in contact with the substrate is at from about 0.1 mm to about 1.5 mm.

11. The method of claim 1 wherein the method further comprises the step of lighting the flow cell from a light source though the flow cell to a recordation device located on the opposite side of the flow cell from the light source.

12. The method of claim 2 wherein the substrate is hair.

13. The method of claim 12 wherein the personal care composition is a shampoo composition and the dilution ratio is from about 1:2 to about 1:10 and a flow rate of about 0.1 to about 0.5 ml/min.

14. The method of claim 12 wherein the personal care composition is a conditioner composition and the dilution ratio is from about 1:70 to about 1:150 and a flow rate of about 0.1 to about 0.5 ml/min.

15. The method of claim 2 wherein the substrate is skin mimic.

16. The method of claim 15 wherein the personal care composition is a skin care composition and the dilution ratio is from about 1:1 to about 1:10 and a flow rate of about 0.1 to about 0.5 ml/min.

17. The method of claim 2 wherein the substrate is fabric.

18. The method of claim 17 wherein the personal care composition is a fabric care composition and the dilution ratio is from about 1:1 to about 1:100 and a flow rate of about 0.1 to about 0.5 ml/min.

* * * * *